United States Patent
Jesudason et al.

(10) Patent No.: US 7,214,697 B2
(45) Date of Patent: May 8, 2007

(54) 2-OXO-BENZIMIDAZOLYL SUBSTITUTED ETHANOLAMINE DERIVATIVES AND THEIR USE AS $\beta_3$ AGONISTS

(75) Inventors: Cynthia Darshini Jesudason, Indianapolis, IN (US); Don Richard Finley, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 113 days.

(21) Appl. No.: 11/228,620

(22) Filed: Sep. 16, 2005

(65) Prior Publication Data
US 2006/0014963 A1    Jan. 19, 2006

Related U.S. Application Data

(62) Division of application No. 10/498,261, filed as application No. PCT/US02/38982 on Dec. 24, 2002, now Pat. No. 7,009,060.

(60) Provisional application No. 60/348,144, filed on Jan. 11, 2002.

(51) Int. Cl.
*A61K 31/4184* (2006.01)
*C07D 213/82* (2006.01)

(52) U.S. Cl. .................. 514/394; 548/306.4
(58) Field of Classification Search ........... 514/394; 548/606.4
See application file for complete search history.

(56) References Cited

U.S. PATENT DOCUMENTS

| | | | |
|---|---|---|---|
| 4,276,304 A | 6/1981 | Ikezaki et al. | |
| 4,826,847 A | 5/1989 | Michel et al. | |
| 5,808,080 A | 9/1998 | Bell et al. | |
| 5,977,154 A | 11/1999 | Bell et al. | |
| 6,011,048 A | 1/2000 | Mathvink et al. | |
| 7,122,680 B2 * | 10/2006 | Jesudason et al. | 548/452 |

FOREIGN PATENT DOCUMENTS

| | | |
|---|---|---|
| DE | 2830884 | 1/1979 |
| EP | 166331 | 1/1986 |
| EP | 221414 | 5/1987 |
| EP | 236624 | 9/1987 |
| EP | 61 1003 | 8/1994 |
| EP | 678511 | 10/1995 |
| EP | 764640 | 3/1997 |
| EP | 827746 | 3/1998 |
| GB | 1549945 | 8/1979 |
| WO | WO 95/29159 | 11/1995 |
| WO | WO 97/10825 | 3/1997 |
| WO | WO 97/46556 | 12/1997 |
| WO | WO 98/04526 | 2/1998 |
| WO | WO 98/09625 | 3/1998 |
| WO | WO 98/32753 | 7/1998 |
| WO | WO 00/40560 | 7/2000 |
| WO | WO 00/44721 | 8/2000 |
| WO | WO 01/07026 | 2/2001 |
| WO | WO 01/35947 | 5/2001 |
| WO | WO 01/36412 | 5/2001 |
| WO | WO 01/53298 | 7/2001 |
| WO | WO 02/06276 | 1/2002 |
| WO | WO 02/38543 | 5/2002 |
| WO | WO 03/016276 | 2/2003 |
| WO | WO 03/016307 | 2/2003 |

OTHER PUBLICATIONS

Lee, et al., J. Het. Chem, vol. 32, No. 1, pp. 1-11 (1995).
Mathvink, Bioorganic & Medicinal Chemistry Letters, vol. 9, No. 13, pp. 1869-1874 (1999).
Shuker, et al., Tetrahedron Letters, vol. 38, No. 35, pp. 6149-6152 (1997).
Weber, et al, Bioorganic & Medicinal Chemistry Letters, vol. 8, No. 9, pp. 1101-1106 (1998).
Weber, et al., Bioorganic & Medicinal Chemistry Letters, vol. 8, No. 16, pp. 2111-2116 (1998).

* cited by examiner

*Primary Examiner*—Kamal A. Saeed
(74) *Attorney, Agent, or Firm*—John C. Demeter; Gilbert T. Voy

(57) ABSTRACT

The present invention relates to a $\beta_3$ adrenergic receptor agonist of formula (I), wherein R is $C_3$–$C_8$ alkyl or ($C_3$–$C_7$ cycloalkyl)$C_1$–$C_5$ alk-di-yl; $R^1$ is H, CN, halo; $C_1$–$C_6$ alkyl, $C_1$–$C_4$ haloalkyl, $CO_2$ $R^6$, $CONR^6R^6$, $NR^6COR^7$, $NR^6R^6$, $OR^6$, $SR^6$, $SOR^7$, $SO_2R^7$ or $SO_2NR^6R^6$; $R^{1a}$ is H, halo or $C_1$–$C_6$ alkyl; $R_2$ is H or $C_1$–$C_6$ alkyl; $R^3$ and $R^4$ are independently H or $C_1$–$C_6$ alkyl $R^5$ is hydrogen, optionally substituted phenyl or optionally substituted heterocycle; X is absent or is $OCH_2$ or $SCH_2$; $X^1$ is absent or $C_1$–$C_5$ alk-di-yl; and $X^2$ is absent or is O, S, NH, $NHSO_2$, $SO_2NH$ or $CH_2$; or a pharmaceutical salt thereof; which is capable of increasing lipolysis and energy expenditure in cells and, therefore, is useful for treating Type 2 diabetes and/or obesity (I)

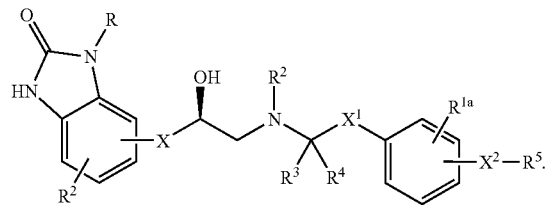

7 Claims, No Drawings

2-OXO-BENZIMIDAZOLYL SUBSTITUTED ETHANOLAMINE DERIVATIVES AND THEIR USE AS $\beta_3$ AGONISTS This application is a Divisional of U.S. application Ser. No. 10/498,261 filed Jun. 9, 2004, now U.S. Pat. No. 7,009,060, which is a national phase application, under U.S.C. Section 371, of PCT/US02/38982 filed Dec. 24, 2002, which claims priority to U.S. Provisional Application No. 60/348,144 filed 11 Jan. 2002.

The current preferred treatment for Type 2, non-insulin dependent diabetes as well as obesity is diet and exercise, with a view toward weight reduction and improved insulin sensitivity. Patient compliance, however, is usually poor. The problem is compounded by the fact that there are currently no approved medications that adequately treat both Type 2 diabetes and obesity.

One therapeutic opportunity that has recently been recognized involves the relationship between adrenergic receptor stimulation and anti-hyperglycemic effects. Compounds that act as $\beta_3$ receptor agonists have been shown to exhibit a marked effect on lipolysis, thermogenesis and serum glucose levels in animal models of Type 2 (non-insulin dependent) diabetes.

The $\beta_3$ receptor, which is found in several types of human tissue including human fat tissue, has roughly 50% homology to the $\beta_1$ and $\beta_2$ receptor subtypes yet is considerably less abundant. Stimulation of the $\beta_1$ and $\beta_2$ receptors can cause adverse effects such as tachycardia, arrhythmia, or tremors. An agonist that is selective for the $\beta_3$ receptor over the $\beta_1$ and $\beta_2$ receptors is, therefore, more desirable for treating Type 2 diabetes or obesity relative to a non-selective agonist.

However, recent studies have suggested the presence of an atypical $\beta$ receptor associated with atrial tachycardia in rats (*Br. J. of Pharmacol.*, 118:2085–2098, 1996). In other words, compounds that are not agonists of the $\beta_1$ and $\beta_2$ receptors can still modulate tachycardia through activation of a yet to be discovered $\beta_4$ receptor or through some other unknown pathway.

A large number of publications have appeared in recent years reporting success in discovery of agents that stimulate the $\beta_3$ receptor. In particular, U.S. Pat. No. 5,786,356 discloses selective $\beta_3$ agonists of the formula:

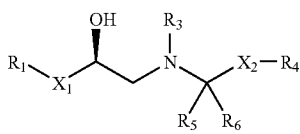

wherein:

$R_1$ can be, among other things, a moiety of the formula:

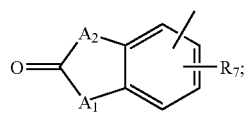

$A_1$ and $A_2$ can be, among other things, NH, NCH$_3$, or NCH$_2$CH$_3$; and $R_4$ can be, among other things, a moiety of the formula:

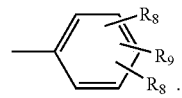

Despite these recent developments, there remains a need to develop a selective $\beta_3$ receptor agonist which has minimal agonist activity against the $\beta_1$ and $\beta_2$ receptors and which displays a minimal propensity to cause atrial tachycardia.

The present invention relates to a compound of formula I:

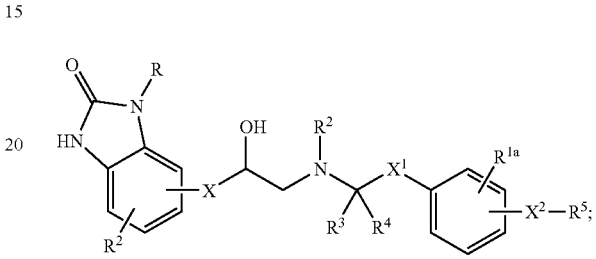

wherein:

R is $C_3$–$C_8$ alkyl or ($C_3$–$C_7$ cycloalkyl)$C_1$–$C_5$ alk-di-yl;

$R^1$ is H, CN, halo, $C_1$–$C_6$ alkyl, $C_1$–$C_4$ haloalkyl, $CO_2R^6$, $CONR^6R^6$, $NR^6COR^7$, $NR^6R^6$, $OR^6$, $SR^6$, $SOR^7$, $SO_2R^7$ or $SO_2NR^6R^6$;

$R^{1a}$ is H, halo or $C_1$–$C_6$ alkyl;

$R_2$ is H or $C_1$–$C_6$ alkyl;

$R^3$ and $R^4$ are independently H or $C_1$–$C_6$ alkyl $R^5$ is hydrogen, optionally substituted phenyl or optionally substituted heterocycle;

X is absent or is $OCH_2$ or $SCH_2$;

$X^1$ is absent or $C_1$–$C_5$ alk-di-yl; and $X^2$ is absent or is O, S, NH, $NHSO_2$, $SO_2NH$ or $CH_2$;

$R^6$ is independently at each occurrence H, $C_1$–$C_6$ alkyl or phenyl; or when two $R^6$ moieties are connected to the same nitrogen atom, then said $R^6$ moieties may combine with the nitrogen to which they are attached to form a pyrollidinyl, piperidinyl or hexamethyleneimino ring; and $R^7$ is $C_1$–$C_6$ alkyl or phenyl; or a pharmaceutical salt thereof.

The present invention also relates to pharmaceutical compositions containing a compound of formula I. In another embodiment, the pharmaceutical compositions of the present invention may be adapted for use in treating Type 2 diabetes and obesity and for agonizing the $\beta_3$ receptor.

The present invention also relates to methods for treating Type 2 diabetes and obesity, as well as a method for agonizing the $\beta_3$ receptor employing a compound of formula I.

In addition, the present invention relates to a compound of formula I for use in treating Type 2 diabetes and obesity as well as a compound of formula I for use in agonizing the $\beta_3$ receptor. The present invention is further related to the use of a compound of formula I for the manufacture of a medicament for treating Type 2 diabetes and obesity as well as for agonizing the $\beta_3$ receptor.

Moreover, the present invention relates to intermediates of formula IV:

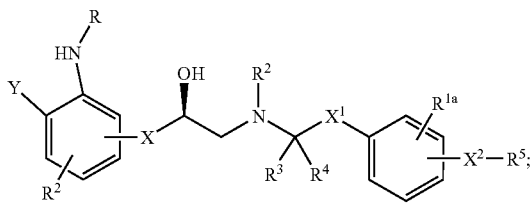

IV wherein Y is nitro or amino and R—R$^5$ and X—X$^2$ are as described above for a formula I compound.

For the purposes of the present invention, as disclosed and claimed herein, the following terms are defined as follows:

The term "C$_3$–C$_8$ alkyl" represents a straight, branched or cyclic hydrocarbon moiety having from three to eight carbon atoms such as n-propyl, isopropyl, cyclopropyl, n-butyl, sec-butyl, t-butyl, cyclobutyl, pentyl, cyclopentyl, hexyl, cyclohexyl, heptyl, cycloheptyl, octyl and the like.

The term "C$_1$–C$_6$ alkyl" represents a straight, branched or cyclic hydrocarbon moiety having from one to six carbon atoms, e.g., methyl, ethyl and the relevant moieties listed above for C$_3$–C$_8$ alkyl. The term "C$_1$–C$_4$ alkyl" refers specifically to methyl, ethyl, n-propyl, isopropyl, cyclopropyl, n-butyl, isobutyl, sec-butyl, t-butyl and cyclobutyl. The term "C$_3$–C$_7$ cycloalkyl" refers specifically to cyclopropyl, cyclobutyl, cyclopentyl, cyclohexyl and cycloheptyl.

The term "halo" represents fluorine, chlorine, bromine, or iodine.

A "C$_1$–C$_4$ haloalkyl" group is a C$_1$–C$_4$ alkyl moiety substituted with up to six halo atoms, preferably one to three halo atoms. An example of a haloalkyl group is trifluoromethyl.

The term "C$_1$–C$_5$ alk-di-yl" refers to a straight or branched chain saturated divalent hydrocarbon moiety of one to five carbon atoms. Examples include but are not intended to be limited to methylene, ethylene, propylene, butylene, pentylene —CH(CH$_3$)CH$_2$—, —CH(C$_2$H$_5$)CH$_2$—, —CH(CH$_3$)CH(CH$_3$)—, —CH$_2$C(CH$_3$)$_2$—, —CH$_2$CH(CH$_3$)CH$_2$—, —C(CH$_3$)$_2$CH$_2$—, and the like.

The term "optionally substituted" as used herein means an optional substitution of one to three groups independently selected from nitro, cyano, phenyl, benzyl, halo, C$_1$–C$_6$ alkyl, C$_1$–C$_4$ haloalkyl, COR$^8$, NR$^9$R$^9$, NR$^9$COR$^8$, NR$^9$SO$_2$R$^{10}$, OR$^9$, OCOR$^8$, OSO$_2$R$^{10}$, SR$^9$, SOR$^{10}$, SO$_2$R$^{10}$ or SO$_2$NR$^9$R$^9$; wherein:

R$^8$ is H, C$_1$–C$_6$ alkyl, phenyl, benzyl, C$_1$–C$_4$ haloalkyl, NR$^{9a}$R$^{9a}$ or OR$^{9a}$;

R$^9$ and R$^{9a}$ are independently H, C$_1$–C$_6$ alkyl or phenyl; or when two R$^9$ or R$^{9a}$ groups are attached to the same nitrogen atom, said R$^9$ or R$^{9a}$ groups, together with the nitrogen to which they are attached, may combine to form a piperidine, pyrrolidine, hexamethyleneimine or morpholine ring; and R$^{10}$ is C$_1$–C$_6$ alkyl or phenyl.

The term "heterocycle" represents a stable, saturated, partially unsaturated, fully unsaturated or aromatic 5 or 6 membered ring, said ring having from one to four heteroatoms that are independently selected from the group consisting of sulfur, oxygen, and nitrogen. The heterocycle may be attached at any point which affords a stable structure. Representative heterocycles include 1,3-dioxolane, 4,5-dibydro-1H-imidazole, 4,5-dihydrooxazole, furan, imidazole, imidazolidine, isothiazole, isoxazole, morpholine, oxadiazole, oxazole, oxazolidinedione, oxazolidone, piperazine, piperidine, pyrazine, pyrazole, pyrazoline, pyridazine, pyridine, pyrimidine, pyrrole, pyrrolidine, tetrazole, thiadiazole, thiazole, thiophene and triazole.

The term "absent" when used to describe the value of a variable, e.g. "X" for a formula I compound, connotes that in the absence of the indicated variable, the adjacent variables on both sides of the absent variable are connected directly together. For example, in the hypothetical chain R$_1$—X$_2$—R$_2$, if X$_2$ is "absent", then the chain becomes R$_1$-R$_2$.

The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof, described herein.

The term "preventing" refers to reducing the likelihood that the recipient of a compound of formula I will incur or develop any of the pathological conditions, or sequela thereof, described herein.

The term "patient" includes human beings and animals such as companion animals (dogs and cats and the like) and livestock animals. Livestock animals are animals raised for food production. The preferred patient of treatment is a human.

As used herein, the term "effective amount" means an amount of a compound of formula I that is capable of treating conditions, or detrimental effects thereof, described herein or that is capable of agonizing the β$_3$ receptor.

The term "selective β$_3$ receptor agonist" means a compound that displays preferential agonism of the β$_3$ receptor over agonism of the β$_1$ or β$_2$ receptor. Thus, β$_3$ selective compounds behave as agonists for the β$_3$ receptor at lower concentrations than that required for similar agonism at the β$_1$ and β$_2$ receptors. A β$_3$ selective compound also includes compounds that behave as agonists for the β$_3$ receptor and as antagonists for the β$_1$ and β$_2$ receptors.

The term "pharmaceutical" when used herein as an adjective means substantially non-deleterious to the recipient patient.

The term "composition", as in pharmaceutical composition, is intended to encompass a product comprising the active ingredient(s) (e.g., a compound of formula I), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutical carrier.

Because certain compounds of the invention contain an acidic moiety (e.g., carboxy), the compound of formula I may exist as a pharmaceutical base addition salt thereof. Such salts include those derived from inorganic bases such as ammonium and alkali and alkaline earth metal hydroxides, carbonates, bicarbonates, and the like. Such salts thus include those derived from calcium, magnesium, potassium or sodium hydroxide. Other salts include those derived from basic organic amines such as aliphatic and aromatic amines, e.g., diethylamine and piperazine; aliphatic diamines, e.g., ethylenediamine; hydroxy alkamines, e.g., diethanolamine and tris(hydroxymethyl)aminomethane; lysine, and the like.

Because certain compounds of the invention contain a basic moiety (e.g., amino), the compound of formula I may also exist as a pharmaceutical acid addition salt. Such salts include those derived from inorganic acids such as hydrochloric, phosphoric and sulfuric acid, and the like, as well as salts derived from organic acids such as acetic, citric, glucuronic, lactic, mandelic, fumaric, glycolic, 1-tartaric, maleic, methanesulfonic, p-toluenesulfonic and succinic acid and like acids. A preferred acid addition salt is the hydrochloride salt.

In the compound of formula I, the following moiety is found:

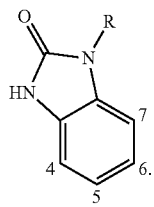

This moiety is a benzimidazol-2-one ring system. The numbers found on the perimeter of the "benz" portion of the pictured moiety represent the numbering system used in the claims and preferred embodiments to describe the positions of the $R^1$ and X substituents.

PREFERRED COMPOUNDS OF THE INVENTION

Certain compounds of formula I are particularly interesting and are preferred. The following listing sets out several groups of preferred compounds. It will be understood that each of the listings may be combined with other listings to create additional groups of preferred compounds. It will be further understood that a preferred formula I group is applicable to a formula IV compound.

a) R is 2,2-dimethylpropyl, cyclopropylmethyl, cyclobutyl-methyl or cyclopentylmethyl;
b) R is cyclopropylmethyl;
c) $R^1$ is H, methyl, ethyl, $CF_3$, chloro or fluoro;
d) $R^1$ is H, methyl, chloro or fluoro;
e) $R^1$ is H or fluoro;
f) $R^1$ is H;
g) $R^{1a}$ is H, methyl, ethyl, $CF_3$, chloro or fluoro;
h) $R^{1a}$ is H, methyl, chloro or fluoro;
i) $R^{1a}$ is H or fluoro;
j) $R^{1a}$ is H;
k) $R^2$ is H;
l) $R^3$ is H or $C_1$–$C_4$ alkyl;
m) $R^4$ is H or $C_1$–$C_4$ alkyl;
n) $R^3$ is H or methyl;
o) $R^4$ is H or methyl;
p) $R^3$ and $R^4$ are both methyl;
q) $R^5$ is selected from hydrogen, phenyl, pyridyl, thienyl, furanyl, pyridazinyl or pyrimidinyl wherein said $R^5$ moieties (except hydrogen) are optionally substituted;
r) $R^5$ is phenyl, pyridyl, thienyl, furanyl, pyridazinyl or pyrimidinyl wherein said $R^5$ moieties are substituted one to three times with fluoro, chloro, cyano, hydroxy, methyl, ethyl, trifluoromethyl, methoxy, ethoxy, amino, $CO_2CH_3$, $CO_2CH_2CH_3$, $CONR^{9a}R^{9a}$, $SCH_3$, $SCH_2CH_3$, $SOCH_3$, $SOCH_2CH_3$, $SO_2CH_3$ or $SO_2CH_2CH_3$;
s) $R^5$ is phenyl, pyridyl, thienyl or furanyl wherein said $R^5$ moieties are substituted one to three times with fluoro, chloro, amino, $CO_2CH_3$, $CO_2CH_2CH_3$, cyano, $CONH_2$, $SO_2CH_3$ or $SO_2CH_2CH_3$;
t) $R^5$ is phenyl, pyridyl, thienyl or furanyl wherein said $R^5$ moieties are substituted once with cyano or $CONH_2$;
u) $R^5$ is phenyl or pyridyl wherein said $R^5$ moieties are substituted once with cyano or $CONH_2$;
v) $R^5$ is pyridyl substituted once with cyano or $CONH_2$;
w) $R^5$ is 5-cyano or 5-carboxamido-pyrid-2-yl;
x) $R^5$ is 4-cyano or 4-carboxamido-phenyl;
y) $R^5$ is 3-cyano or 3-carboxamido-pyrid-2-yl;
z) $R^5$ is 2-cyano or 2-carboxamido-phenyl;
aa) X is connected to the benzimidazol-2-one ring system at the 7-position of said system;
bb) X is $OCH_2$;
cc) $X^1$ is a bond, methylene or ethylene;
dd) $X^1$ is methylene;
ee) $X^2$ is at the para-position relative to $X^1$;
ff) $X^2$ is a bond or O;
gg) $X^2$ is O;
hh) $R^{9a}$ is independently at each occurrence H or methyl;
ii) the compound of formula I is an acid addition salt;
jj) the compound of formula I is the hydrochloride salt;

Synthesis

The compounds of formula I may be prepared as described in the following Schemes and Examples.

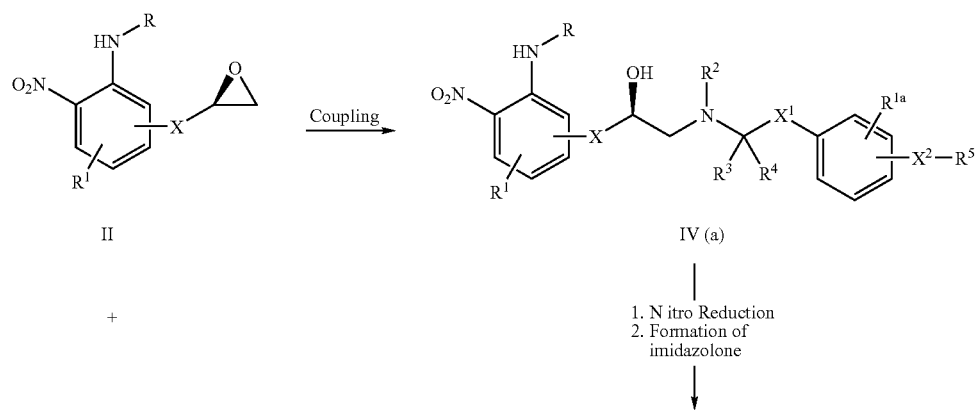

Scheme I

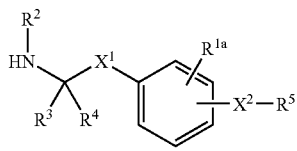

III

Formula I compound

The compound of formula IV may be prepared by methods appreciated in the art for the amination of epoxides, see, e.g., PCT Patent Publication WO 01/06276, the teachings of which are herein incorporated by reference. For example, an epoxide of formula II may be combined with an amine of formula III in a lower alcohol such as ethanol, isopropanol, n-butanol or t-butanol; dimethylformamide; or dimethylsulfoxide, preferably, at room temperature to the reflux temperature of the reaction mixture to give the compound of formula IV. The reaction may also be carried out under conditions generally described in Atkins, et al., Tet. Let., 27:2451, 1986.

The nitro group found on the nitroaniline compound of formula IV may be reduced by standard reduction chemistry known in the art, for example, via hydrogenation or by using sodium dithionite as described below to afford the corresponding diamino compound. The diamino product may be converted to the compound of formula I via standard acylation chemistry known in the art, for example, with carbonyldiimidazole or triphosgene as described below to form the imidazol—2-one ring. Relevant acylation and reduction chemistry known in the art may be found in, e.g., Larock, "Comprehensive Organic Transformations: A Guide to Functional Group Preparations", VCH Publishers, New York, N.Y., 1989 (Larock).

The epoxide starting materials employed in Scheme 1 (formula II compound) may be prepared by techniques recognized and appreciated by one skilled in the art. To illustrate, epoxides of formula II, where X is $OCH_2$ or $SCH_2$ may be prepared according to the procedures detailed in Scheme 2 wherein Pg is hydrogen or a protecting group and X' is O or S. See, e.g., T. W. Greene and P. Wuts, "Protective Groups in Organic Synthesis", John Wiley and Sons, New York, N.Y., 1991 for commonly employed protecting groups and methods for their attachment and removal.

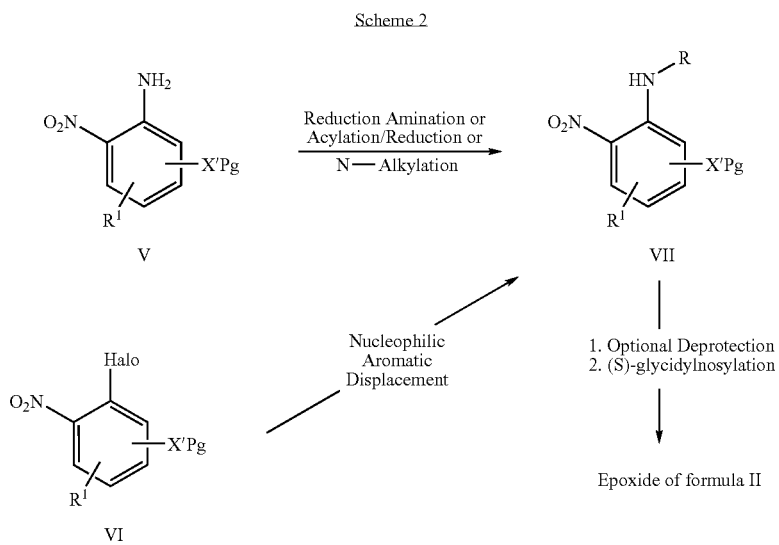

Scheme 2

Epoxides of formula II may be prepared starting with an aminonitrophenol of formula V, such as for example, 2-amino-3-nitrophenol. Attachment of the claimed "R" groups to the amino moiety may be accomplished via reductive amination (one-pot conversion), acylation chemistry followed by reduction chemistry (two step conversion), or via N-alkylation chemistry under conditions appreciated in the art for such transformations to give the compound of formula VII.

The N-alkylation chemistry described in Scheme 2 may be employed to prepare those compounds of formula VII wherein R does not have a methylene alpha to the imidazole nitrogen, e.g., wherein R is isopropyl. When R does have an alpha-methylene, e.g., when R is cyclohexylmethyl, said R group is preferably attached via reductive amination chemistry or acylation/reduction techniques described above.

In the case where the X' group is unprotected (X' is H), an acylation reaction may also result in acylation on the —X'H group. In the event that an unprotected X' group is acylated, the X' acyl group may be selectively removed using an aqueous base. When performing N-alkylation chemistry, it is preferable to employ a hydroxy or thiol protecting group as known in the art (see Green).

A compound of formula VII may also be prepared from a halo-, preferably fluoro-, substituted nitrophenol of formula VI via aromatic nucleophilic displacement with an amine of the formula RNH.

The compound of formula VII, however obtained, may then be reacted with S-glycidylnosylate as described below or as described in U.S. Pat. No. 5,786,356, the teachings of which are herein incorporated by reference, to give the epoxide of formula II.

Amines of formula III may be prepared as described in the previously incorporated by reference WO 01/06276, or in the Preparations below, or by analogous procedures known in the art.

Compounds of formula V, VI, RNH and other reagents described above are either commercially available, known in the art, or can be prepared by methods known in the art or described herein.

The following Preparations, Examples and Formulations are provided so that the invention might be more fully understood. They should not be construed as limiting the invention in anyway.

Preparations

Epoxides of Formula II

Epoxides 1–5 are prepared for use as described in Scheme 1. These epoxides are pictured below in Table 1.

TABLE 1

1
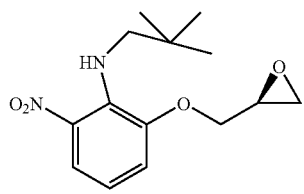

2
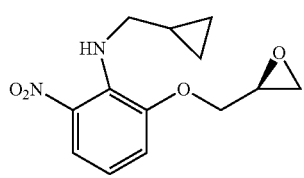

3
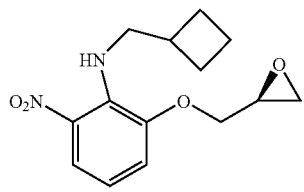

4
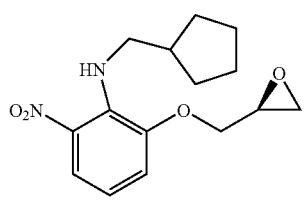

TABLE 1-continued

5
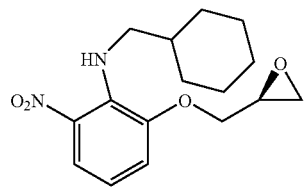

Epoxiode 1

A solution of 2-amino-3-nitrophenol (10.0 g, 64.9 mmol) in $CH_2Cl_2$ (200 mL) at 0° C. is treated with triethylamine (22.6 mL, 162.2 mmol), followed by pivaloyl anhydride (28.9 mL, 142.7 mmol). The reaction is warmed to room temperature and then heated at reflux overnight. The reaction mixture is quenched by addition of water. The aqueous layer is extracted several times with $CH_2Cl_2$, dried over $MgSO_4$ and concentrated.

This crude material is taken up in methanol (300 mL), $K_2CO_3$ added (3.0 g, 21.7 mmol) and the mixture stirred at room temperature for 24 hours. The reaction is quenched by addition of 1N HCl, and the mixture is extracted several times with ethyl acetate, dried over $MgSO_4$, and filtered through a pad of silica gel to provide the desired 2-pivalylamido-3-nitrophenol (14.3 g, 92.8%, two steps).

The pivalylamide (7.1 g, 29.9 mnol) in tetrahydrofuran (150 mL) is cooled to 0° C., and $BH_3 \cdot CH_3S$ (7.5 mL, 74.9 mmol) is added slowly. The ice bath is removed and the reaction stirred at room temperature for 1 hour. The reaction mixture is carefully acidified with 1N HCl, and stirred for 1 hour at room temperature. Saturated $NaHCO_3$ is then added until the pH is basic, and the mixture is extracted twice with ethyl acetate. The organic layer is washed with brine, dried over $MgSO_4$, filtered and evaporated. The desired phenol is obtained after flash chromatography using 25% ethyl acetate/hexanes.

The phenol (1.5 g, 6.7 mmol), potassium carbonate (1.0 g, 7.4 mmol) and (S)-glycidylnosylate are combined in acetone (20 mL), heated at reflux for 18 hours, cooled to room temperature and the solids are removed via filtration. The filtrate is concentrated and the crude product purified on silica gel (10% ethyl acetate/hexane) to give 1.7 g of the title epoxide.

Epoxide 2

The title epoxide is prepared from 2-amino-3-nitrophenol (5.0 g, 32.4 mmol) by the procedure described above for Epoxide 1 except that cyclopropyl carbonyl chloride (6.5 mL, 71.4 mmol) is used instead of the corresponding acid anhydride in the first step of the synthesis.

Epoxide 3

The title epoxide is prepared from 2-amino-3-nitrophenol (5.4 g, 35.0 mmol) by the procedure described above for Epoxide 2 except that reaction is run at room temperature and cyclobutane carbonyl chloride (8.8 mL, 77 mmol) is used instead of cyclopropyl carbonyl chloride in the first step of the synthesis.

Epoxide 4

The title epoxide is prepared from 2-amino-3-nitrophenol (11.2 g, 73.0 mmol) by the procedure described above for Epoxide 2 except that reaction is run at room temperature and cyclopentane carbonyl chloride (19.5 mL, 160 mmol) is used instead of cyclopropyl carbonyl chloride in the first step of the synthesis.

Epoxide 5

2-Amino-3-nitrophenol (2.0 g, 13.0 mmol), cyclohexane carboxaldehyde (2.9 g, 25.9 mmol), sodium triacetoxyborohydride (7.7 g, 36.3 mmol) and acetic acid (4.6 g, 77.8 mmol) are mixed in 1,2 dichloroethane (30 mL) and stirred a room temperature for 2 days. The reaction is quenched by addition of water. The mixture is extracted several times with ethyl acetate, dried over MgSO₄ and evaporated. The crude material is purified using flash chromatography (10% ethyl acetate/hexanes) to provide 1.62 g of the N-alkylated phenol (49.9%).

The phenol is treated with (S)-glycidylnosylate as described for Epoxide 1, to provide 1.0 g of the title epoxide (50%).

Amines of Formula III

Amines 1–4 are prepared for use as described in Scheme 1. These amines are pictured below in Table 2.

TABLE 2

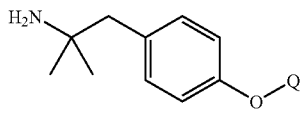

Q =

| | |
|---|---|
| 1 | 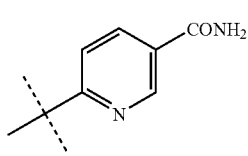 |
| 2 | 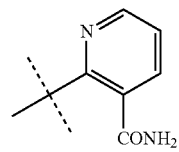 |

TABLE 2-continued

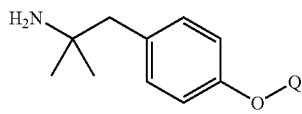

Q =

| | |
|---|---|
| 3 | 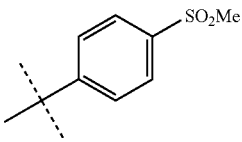 |
| 4 | 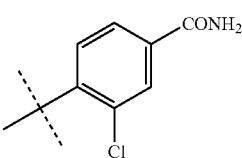 |

EXAMPLES

Nitroaniline Compounds of Formula IV

Representative Procedure 1: Amination of Epoxide

A stirred mixture of an epoxide of formula II (1 equivalent) and an amine of formula III (2 equivalents) in ethanol is heated at reflux overnight. The solvent is evaporated to dryness to give a crude oil that is purified by flash chromatography using either ethyl acetate/hexanes mixtures or 0–10% CH₃OH/CH₂Cl₂/0.1–1% NH₄OH. Preparation of desired product is confirmed via mass spectral analysis (MSA).

Nitroaniline 1

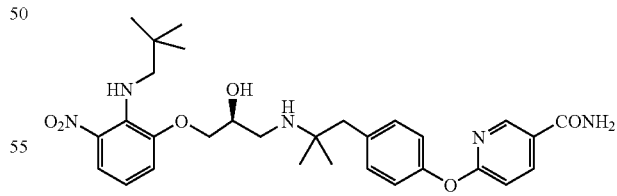

Nitroaniline 1 is prepared via a procedure substantially analogous to Representative Procedure 1 except that the reaction is stirred at reflux for 30 hours and the crude material is purified by flash chromatography (10% 25:5:1 CHCl₃/CH₃OH/NH₄OH with 90% 9:1 CHCl₃/CH₃OH). MSA=566.6.

Nitroanilines 2–11 are prepared via procedure substantially analogous to Representative Procedure 1.

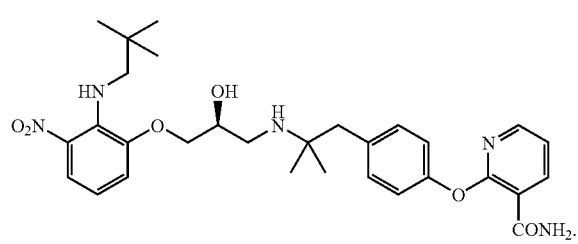
MSA = 566.28
Nitroaniline 2
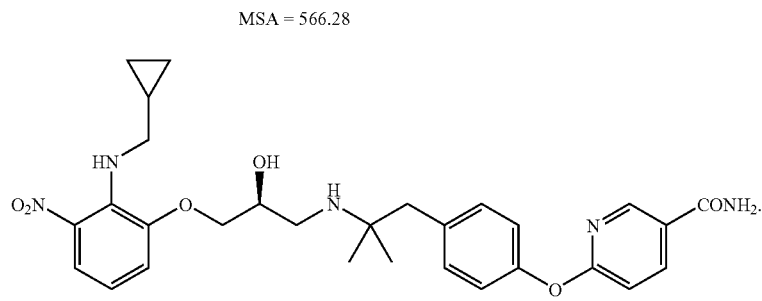
MSA = 550.2
Nitroaliline 3
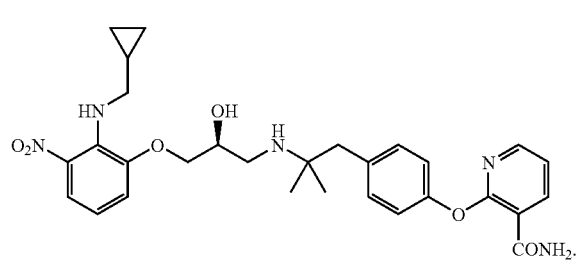
MSA = 550.25
Nitroaliline 4
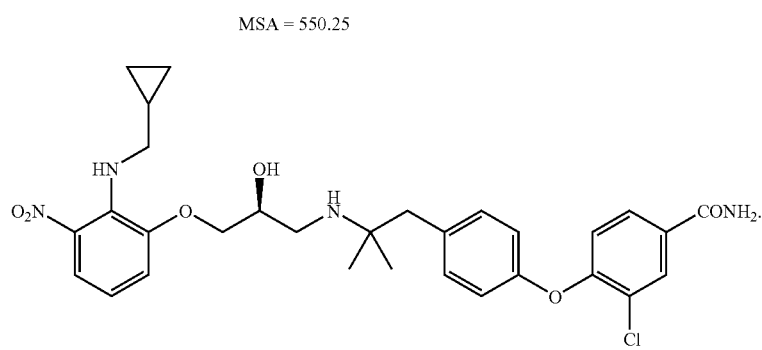
MSA = 583.2
Nitroaliline 5
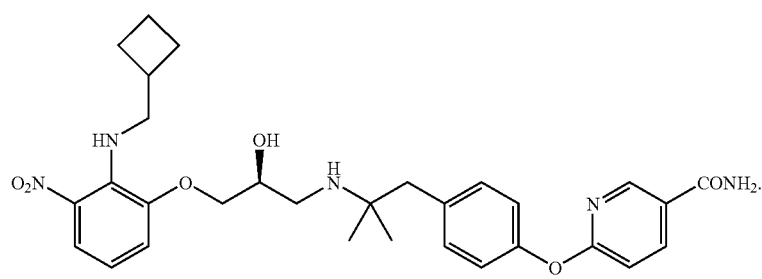
MSA = 564.3
Nitroaline 6

-continued
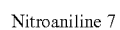
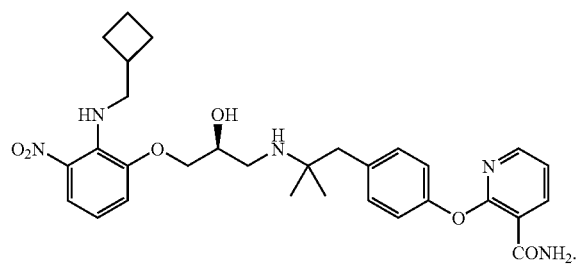
MSA = 564.3
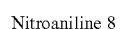
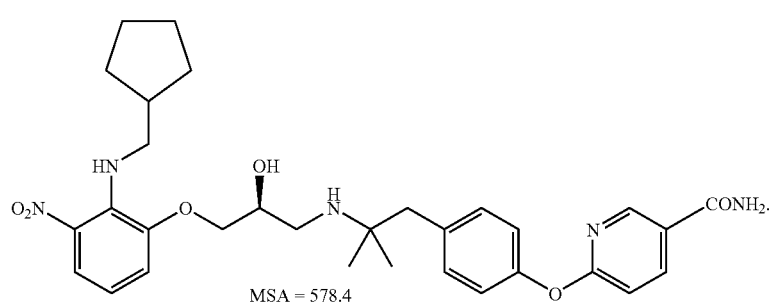
MSA = 578.4
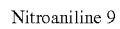
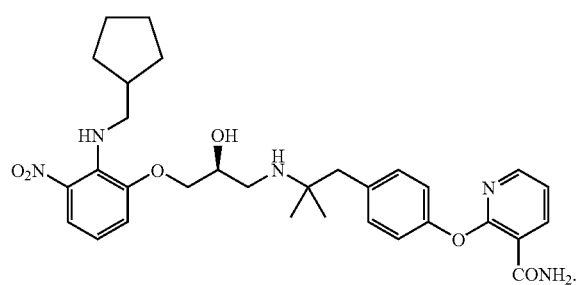
MSA = 578.4
Nitroaniline 10
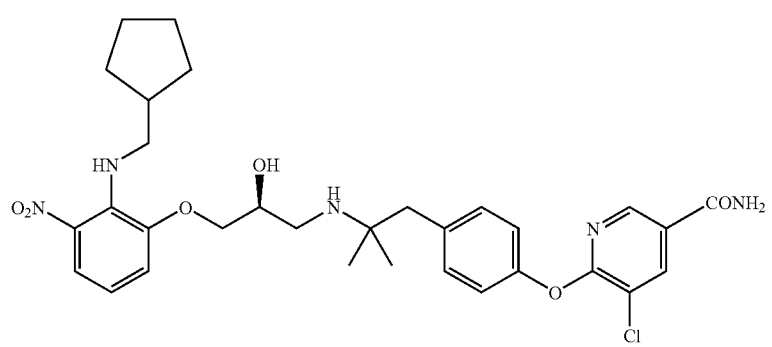
MSA = 611.4

-continued

Nitroaniline 11

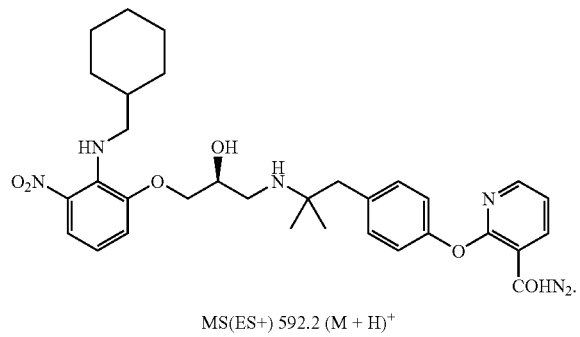

MS(ES+) 592.2 (M + H)+

Compounds of Formula I

Representative Procedure 2: Reduction and Imidazolone Formation

The product of Representative Procedure 1 is dissolved in a 1:1 mixture of ethanol and water, NaHCO$_3$ (6 equivalents) is added, followed by Na$_2$S$_2$O$_4$ (6 equivalents). When reaction mixture turns colorless, the solution is filtered and evaporated to give a residue. This residue is suspended in 1:1 mixture of toluene/1N HCl, triphosgene (2–5 equivalents) is added and the reaction stirred at room temperature for 18–72 hours. The reaction is worked up either by decanting off the liquid, or concentrating in vacuo, or adjusting pH to 8–9 with NaHCO$_3$ or NaOH, extracting with ethyl acetate/tetrahydrofuran and separating organic layer, drying (Na$_2$SO$_4$), then concentrating in vacuo to give crude product.

The crude material is purified either by flash chromatography (25:5:1 CHCl$_3$/MeOH/NH$_4$OH, or 0–10% MeOH/CH$_2$Cl$_2$/1% NH$_4$OH) or by reverse phase chromatography (acetonitrile/water/0.01% HCl) to yield the desired material. Preparation of desired product is confirmed via MSA.

Emax±Standard Error Mean (SEM) data, discussed in the "Demonstration of Function" section below, is also included for the following compounds where available. The Emax values represent the average of at least 3 runs except as otherwise indicated.

Example 12

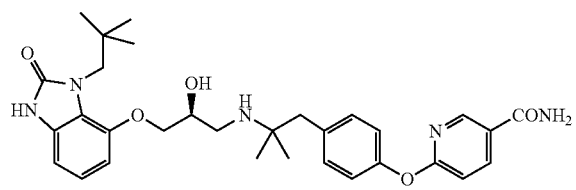

Nitroaniline 1 (1.87 g, 3.3 mmol) is dissolved in a 1:1 mixture of ethanol and water (60 mL each). NaHCO$_3$ (1.67 g, 19.8 mmol) is added, followed by Na$_2$S$_2$O$_4$ (3.5 g, 19.8 mmol). The reaction mixture is stirred at room temperature for approximately 10 minutes. The color of the reaction mixture is changed from orange to colorless. MS data indicates the formation of the desired dianiline. MS(ES+) 536.4 (M+H)+. The solution is filtered and evaporated to give a gummy residue.

This residue is suspended in toluene (120 mL) and 1N HCl (120 mL), triphosgene is added (4.9 g, 16.5 mmol) and the resulting mixture is stirred overnight. The reaction is worked up by decanting off the liquid and concentrating in vacuo to give crude product. The crude material is purified by flash chromatography (25:5:1 CHCl$_3$/CH$_3$OH/NH$_4$OH) to give 780 mg (42%) of the title compound. MS(ES+) 562.1 (M+H)+. Emax (SEM)=65.5 (3.1).

Example 13

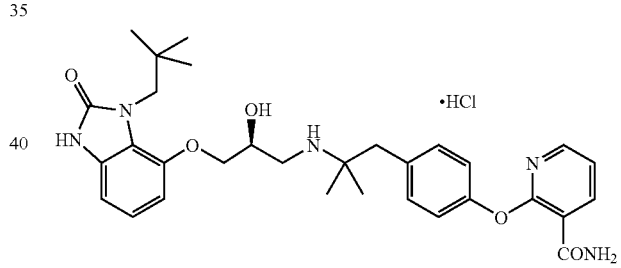

Nitroaniline 2 (0.69 g, 1.2 mmol) is dissolved in a 1:1 mixture of ethanol and water (30 mL each). NaHCO$_3$ (0.62 g, 7.3 mmol) is added, followed by Na$_2$S$_2$O$_4$ (1.3 g, 7.3 mmol). The reaction mixture is stirred at room temperature for 3 hours. The color of the reaction mixture is changed from orange to colorless. MSA indicates the formation of the desired dianiline (MS(ES+) 536.4 (M+H)+). The solution is filtered and evaporated to give a gummy residue. The residue is suspended in toluene (60 mL) and 1N HCl (60 mL), triphosgene is added (0.73 g, 2.68 mmol) and the mixture is stirred for 3 days. The reaction is worked up by decanting off the liquid and concentrating in vacuo to give crude product. The crude material is purified by flash chromatography (10:1:0.1 CH$_2$Cl$_2$/CH$_3$OH/NH$_4$OH to yield 380 mg of the free base of the title compound (55%).

A cold CH$_3$OH solution of this free base is then treated with 1.1 equivalents of 1 M HCl/diethyl ether, concentrated, triturated in diethyl ether, filtered, and dried to give the title compound. MS(ES+) 562.28 (M+H)+. Emax (SEM)=66.4 (4.0).

Example 14

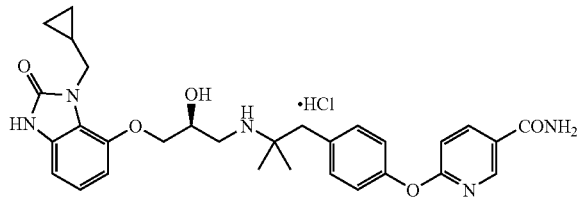

Nitroaniline 3 is converted to crude title compound via the procedure described in Representative Procedure 2. The crude material is purified by reverse phase chromatography (acetonitrile/water/0.01% HCl) to give 63 mg of the title compound. MS(ES+) 546.3 (M+H)$^+$. Emax (SEM)=67.9 (6.4).

Example 15

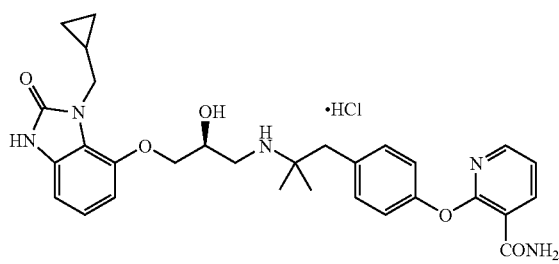

Nitroaniline 4 is converted to crude title compound via the procedure described in Representative Procedure 2. The crude material is purified by reverse phase chromatography (acetonitrile/water/0.01% HCl) to give the desired compound (HCl salt, 257 mg, 31%) as a white solid. MS (ES+) 546.27 (M+H)$^+$. Emax (SEM)=80.1 (4.4).

Example 16

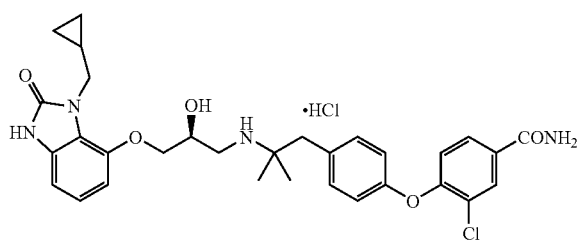

Nitroaniline 5 is converted to crude title compound via the procedure described in Representative Procedure 2. The crude material is purified by chromatography (SiO$_2$, 0–10% CH$_3$OH/CH$_2$Cl$_2$/1% NH$_4$OH) to give the free base of the title compound. A cold CH$_3$OH solution of the free base is then treated with 1.1 equivalents of 1 M HCl/Et$_2$O, concentrated, triturated in diethyl ether, filtered, and dried to give 23 mg of the title compound (4%). MS(ES+) 579.2(M+H)$^+$. Emax (SEM)=76.0 (6.5).

Example 17

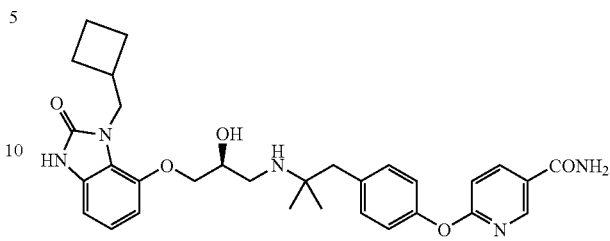

Nitroaniline 6 is converted to crude title compound via the procedure described in Representative Procedure 2. The crude material is-purified by chromatography (SiO$_2$, 0–10% CH$_3$OH/CH$_2$Cl$_2$/1% NH$_4$OH) to give 200 mg of the title compound (40%). MS(ES+)560.3(M+H)$^+$. Emax (SEM)=58.2 (2.0).

Example 18

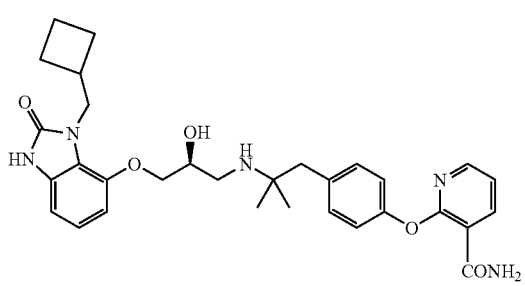

Nitroaniline 7 is converted to crude title compound via the procedure described in Representative Procedure 2. The crude material is purified by chromatography (SiO$_2$, 0–10% CH$_3$OH/CH$_2$Cl$_2$/1% NH$_4$OH) to give 280 mg of the title compound (33%). MS(ES+) 560.3(M+H)$^+$. Emax (SEM)=59.8 (7.1).

Example 19

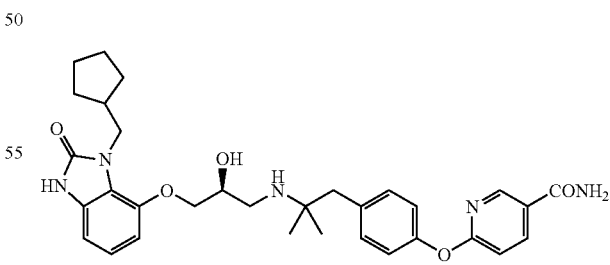

Nitroaniline 8 is converted to crude title compound via the procedure described in Representative Procedure 2. The crude material is purified by chromatography (SiO$_2$, 0–10% CH$_3$OH/CH$_2$Cl$_2$/1% NH$_4$OH) to give 50 mg of the title compound (22%). MS (ES+) 574.3(M+H)$^+$. Emax (SEM)=63.7 (2.6).

Example 20

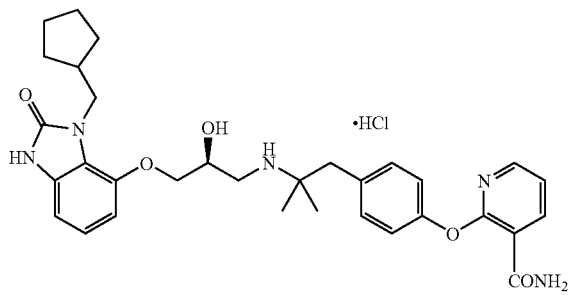

Nitroaniline 9 is converted to crude title compound via the procedure described in Representative Procedure 2. The crude material is purified by reverse phase chromatography (acetonitrile/water/0.01% HCl) to give 93 mg of the title compound (8%). MS(ES+) 574.4 (M+H)$^+$. Emax (SEM) =66.8 (1.7).

Example 21

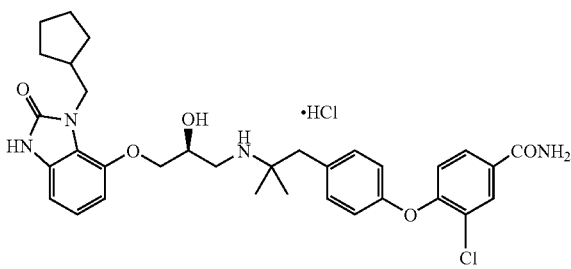

Nitroaniline 10 is converted to crude title compound via the procedure described in Representative Procedure 2 except tetrahydrofuran is used as a co-solvent. The crude material is purified by reverse phase chromatography (acetonitrile/water/0.01% HCl) to give 80 mg of the title compound (39%). MS(ES+) 607.2 M$^+$. Mp=159–164(dec)° C. Emax (SEM)=64.7,(1.5).

Demonstration of Function

The genes encoding the human $\beta_1$-adrenergic receptor (Frielle et al., *Proc. Natl. Acad. Sci.*, 84:7920–7924, 1987), the human $\beta_2$-adrenergic receptor (Kobika et al., *Proc. Natl. Acad. Sci.*, 84:46–50, 1987, Emorine et al., *Proc. Natl. Acad. Sci.*, 84:6995–6999, 1987) and the human $\beta_3$ adrenergic receptor (GraTineman et al., *Molecular Pharmacology*, 44(2):264–70, 1993) are individually subcloned into a phd expression vector (Grinnell el al., *Bio/Technology*, 5:1189–1192, 1987) and transfected into the DXB-11 Chinese hamster ovary (CHO) cell line by calcium phosphate precipitation methodology. The stably transfected cells are grown to 95% confluency in 95% Dulbecco's modified Eagles Medium (DMEM), 5% fetal bovine serum and 0.01% proline. Media is removed and the cells are washed with phosphate buffered (pH 7.4) saline (without magnesium and calcium). Cells are then lifted using an enzyme free cell dissociation solution (Specialty Media, Lavallette, N.J.) and pelleted by centrifugation.

Cells from each of the above cell lines are resuspended and added (20,000/well) to a 96-well plate. Cells are incubated at 37° C. with representative compounds of the invention for 20 minutes in buffer (Hank's balanced salt solution, 10 mM HEPES, 0.1% BSA, 1 mM L-ascorbic acid, 0.2% dimethyl sulfoxide, 1 mM 3-isobutyl-1-methylxanthine, pH 7.4). After halting the incubation with quench buffer (50 mM Na Acetate, 0.25% Triton X-100, pH 5.8), the c-AMP level is quantified by scintillation proximity assay (SPA) using a modification of the commercially available c-AMP kit (Amersham, Arlington Heights, Ill.) with rabbit anti-cAMP antibody (ICN Bioniedicals, Aurora, Ohio) for the kit.

Sigmoidal dose response curves, from the whole cell receptor coupled c-AMP assay are fit to a four parameter logistic equation using non linear regression: y=(a-d)/(1+(Dose/c)$^b$)+d where a and d are responses at zero and maximal dose, b is the slope factor and c is the EC$_{50}$ as previously described (DeLean et al., *Am. J. Physiol.*, 235, E97–E102, 1978). EC$_{50}$ is assessed as the concentration producing 50% of the maximum response to each agonist.

Isoproterenol is accepted in the art as a non-selective $\beta_3$ agonist and is widely used as a comparator in evaluating the activity of compounds. See *Trends in Pharm. Sci.*, 15:3, 1994. The % intrinsic activity (E$_{max}$) of representative compounds of the invention is assessed relative to isoproterenol by the compound's maximal response divided by the isoproterenol maximal response times 100.

In Vitro Rat Atrial Tachycardia

Male rats (250–350 g) (Harlan Sprague Dawley, Indianapolis, Ind., USA) are killed by cervical dislocation. Hearts are removed and the left and right atria are dissected and mounted with thread in tissue baths containing 10 mls of modified Krebs' solution. Initial resting tension is 1.5–2.0 g at the outset of the experiment (*Naunyn-Schmied Arch. Pharmacol.*, 320:145, 1982). Tissues are allowed to equilibrate approximately 30 minutes with vigorous oxygenation before exposure to a compound of the invention.

To evaluate the ability of test compounds to increase heart rate, representative compounds of the present invention are added cumulatively once the atrial rate reached a steady state from the previous addition. Compound addition is continued until no further increase in atrial rate occurred or until a concentration of 10$^{-4}$ is reached. The increase in beats per minute (bpm) is measured for each concentration of test compound by means of a BioPac System (*Br. J. of Pharmacol.*, 126:1018–1024, 1999).

Table 3 shows atrial tachycardia data for compounds of the present invention (4$^{th}$ through 8$^{th}$ entries) versus certain corresponding compounds generically disclosed in U.S. Pat. No. 5,786,356 (entries 1–3). The "% increase" values represent the average of at least 3 runs. Relative to these compounds generically disclosed in U.S. Pat. No. 5,786,356, the compounds of the present invention exhibit a significantly reduced stimulation of atrial tachycardia.

TABLE 3

In vitro Rat Atrial Tachycardia Data

| R | % Increase in Heart Rate |
|---|---|
| Hydrogen | 17.7 ± 3.7 |
| Methyl | 20.8 ± 1.8 |
| Ethyl | 19.9 ± 0.4 |
| 2,2-Dimethylpropyl | 4.6 ± 0.2 |
| Cyclopropylmethyl | 8.9 ± 1.2 |
| Cyclobutylmethyl | 6.5 ± 2.2 |
| Cyclopentylmethyl | 9.9 ± 0.3 |

Utilities

As agonists of the $\beta_3$ receptor, a compound of the present invention is useful in treating conditions in humans and animals in which the $\beta_3$ receptor has been demonstrated to play a role. The diseases, disorders or conditions for which compounds of the present invention are useful in treating include, but are not limited to, (1) diabetes mellitus, (2) hyperglycemia, (3) obesity, (4) hyperlipidemia, (5) hypertriglyceridemia, (6) hypercholesterolemia, (7) atherosclerosis of coronary, cerebrovascular and peripheral arteries, (8) gastrointestinal disorders including peptid ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (9) neurogenic inflammation of airways, including cough, asthma, (10) depression, (11) prostate diseases such as benign prostate hyperplasia, (12) irritable bowel syndrome and other disorders needing decreased gut motility, (13) diabetic retinopathy, (14) neuropathic bladder dysfunction, (15) elevated intraocular pressure and glaucoma and (16) non-specific diarrhea dumping syndrome.

In treating non-companion animals, the compounds of the present invention are useful for increasing weight gain and/or improving the feed utilization efficiency and/or increasing lean body mass and/or decreasing birth mortality rate and increasing post/natal survival rate.

Formulation

The compound of formula I is preferably formulated prior to administration. Therefore, yet another embodiment of the present invention is a pharmaceutical composition comprising a compound of formula I and a pharmaceutical carrier.

The present pharmaceutical compositions are prepared by known procedures using well-known and readily available ingredients. In making the formulations of the present invention, the active ingredient (e.g., formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or Medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

FORMULATION EXAMPLES

Formulation 1

| Tablets | |
|---|---|
| Ingredient | Quantity (mg/tablet) |
| Active Ingredient | 5–500 |
| Cellulose, microcrystalline | 200–650 |
| Silicon dioxide, fumed | 10–650 |
| Stearate acid | 5–15 |

The components are blended and compressed to form tablets.

Formulation 2

| Suspensions | |
|---|---|
| Ingredient | Quantity (mg/5 ml) |
| Active Ingredient | 5–500 mg |
| Sodium carboxymethyl cellulose | 50 mg |
| Syrup | 1.25 mg |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Formulation 3

| Intravenous Solution | |
|---|---|
| Ingredient | Quantity |
| Active Ingredient | 25 mg |
| Isotonic saline | 1,000 ml |

The solution of the above ingredients is intravenously administered to a patient at a rate of about 1 ml per minute.

Dose

The specific dose administered is determined by the particular circumstances surrounding each situation. These circumstances include, the route of administration, the prior medical history of the recipient, the pathological condition or symptom being treated, the severity of the condition/symptom being treated, and the age and sex of the recipient. However, it will be understood that the therapeutic dosage administered will be determined by the physician in the light of the relevant circumstances.

Generally, an effective minimum daily dose of a compound of formula I is about 5, 10, 15, or 20 mg. Typically, an effective maximum dose is about 500, 100, 60, 50, or 40 mg. Most typically, the dose ranges between 15 mg and 60 mg. The exact dose may be determined, in accordance with the standard practice in the medical arts of "dose titrating" the recipient; that is, initially administering a low dose of the compound, and gradually increasing the does until the desired therapeutic effect is observed.

Route of Administration

The compounds can be administered by a variety of routes including the oral, rectal, transdermal, subcutaneous, topical, intravenous, intramuscular or intranasal routes.

Combination Therapy

A compound of formula I may be used in combination with other drugs that are used in the treatment/prevention/suppression or amelioration of the diseases or conditions for which compounds of formula I are useful, e.g., treatment of obesity and/or type 2 diabetes. Such other drug(s) may be administered, by a route and in an amount commonly used therefor, contemporaneously or sequentially with a compound of formula I. When a compound of formula I is used contemporaneously with one or more other drugs, a pharmaceutical unit dosage form containing such other drugs in addition to the compound of formula I is preferred. Accordingly, the pharmaceutical compositions of the present invention include those that also contain one or more other active ingredients, in addition to a compound of formula I.

We claim:

1. A compound of formula I:

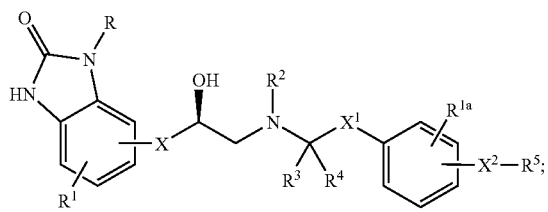

I wherein:
R is $C_3$–$C_8$ alkyl or ($C_3$–$C_7$ cycloalkyl)$C_1$–$C_5$ alk-di-yl;
$R^1$ is H, CN, halo, $C_1$–$C_6$ alkyl, $C_1$–$C_4$ haloalkyl, $CO_2R^6$, $CONR^6R^6$, $NR^6COR^7$, $NR^6R^6$, $OR^6$, $SR^6$, $SOR^7$, $SO_2R^7$ or $SO_2NR^6R^6$;
$R^{1a}$ is H, halo or $C_1$–$C_6$ alkyl;
$R_2$ is H or $C_1$–$C_6$ alkyl;
$R^3$ and $R^4$ are independently H or $C_1$–$C_6$ alkyl
$R^5$ is hydrogen, optionally substituted phenyl or optionally substituted heterocycle;
X is absent or is $OCH_2$ or $SCH_2$;
$X^1$ is absent or $C_1$–$C_5$ alk-di-yl; and
$X^2$ is absent or is O, S, NH, $NHSO_2$, $SO_2NH$ or $CH_2$;
$R^6$ is independently at each occurrence H, $C_1$–$C_6$ alkyl or phenyl; or when two $R^6$ moieties are connected to the same nitrogen atom, then said $R^6$ moieties may combine with the nitrogen to which they are attached to form a pyrollidinyl, piperidinyl or hexamethyleneimino ring; and
$R^7$ is $C_1$–$C_6$ alkyl or phenyl; or a pharmaceutical salt thereof.

2. The compound of claim 1 of the formula:

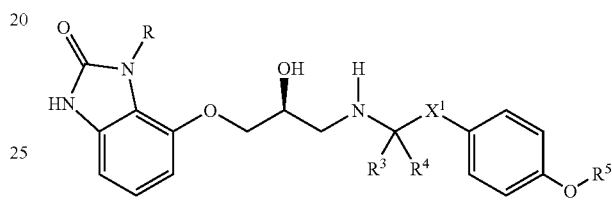

wherein:
$R^3$ is H or $C_1$–$C_4$ alkyl;
$R^4$ is H or $C_1$–$C_4$ alkyl;
$R^5$ is selected from hydrogen, phenyl, pyridyl, thienyl, furanyl, pyridazinyl or pyrimidinyl wherein said $R^5$ moieties (except hydrogen) are optionally substituted; and
$X^1$ is a bond, methylene or ethylene; or a pharmaceutical salt thereof.

3. The compound of claim 2 wherein:
R is 2,2-dimethylpropyl, cyclopropylmethyl, cyclobutylmethyl or cyclopentylmethyl;
$R^3$ and $R^4$ are both methyl;
$X^1$ is methylene; and
$R^5$ is phenyl, pyridyl, thienyl or furanyl wherein said $R^5$ moieties are substituted one to three times with fluoro, chloro, amino, $CO_2CH_3$, $CO_2CH_2CH_3$, cyano, $CONH_2$, $SO_2CH_3$ or $SO_2CH_2CH_3$; or a pharmaceutical salt thereof.

4. The compound of claim 3 wherein $R^5$ is pyridyl substituted once with cyano or $CONH_2$.

5. The compound of claim 4 which is the hydrochloride salt.

6. A method of treating Type 2 Diabetes comprising administering to a patient in need thereof a compound of claim 1.

7. A method of treating obesity comprising administering to a patient in need thereof a compound of claim 1.

* * * * *